United States Patent
Franke et al.

(10) Patent No.: US 10,782,367 B2
(45) Date of Patent: Sep. 22, 2020

(54) MPI METHOD AND SYSTEM FOR VISUALLY REPRESENTING MPI IMAGE DATA

(71) Applicant: Bruker BioSpin MRI GmbH, Ettlingen (DE)

(72) Inventors: Jochen Franke, Karlsruhe (DE); Michael Herbst, Freiburg (DE)

(73) Assignee: BRUKER BIOSPIN MRI GMBH, Ettlingen (DE)

( * ) Notice: Subject to any disclaimer, the term of this patent is extended or adjusted under 35 U.S.C. 154(b) by 0 days.

(21) Appl. No.: 16/351,743

(22) Filed: Mar. 13, 2019

(65) Prior Publication Data
US 2019/0285710 A1    Sep. 19, 2019

(30) Foreign Application Priority Data

Mar. 13, 2018 (DE) .......................... 10 2018 203 783

(51) Int. Cl.
*G01R 33/12* (2006.01)
*G06F 17/16* (2006.01)
(Continued)

(52) U.S. Cl.
CPC ............ *G01R 33/1276* (2013.01); *A61B 5/05* (2013.01); *A61B 5/0515* (2013.01); *A61B 90/00* (2016.02);
(Continued)

(58) Field of Classification Search
CPC .... G01R 33/1276; G01R 33/00; A61B 90/00; A61B 5/05; A61B 5/015; G16H 30/20; G16H 30/40; G06F 17/16
See application file for complete search history.

(56) References Cited

U.S. PATENT DOCUMENTS

| | | |
|---|---|---|
| 9,364,165 B2 | 6/2016 | Gleich |
| 10,261,141 B2 | 4/2019 | Tonyushkin |
| (Continued) | | |

FOREIGN PATENT DOCUMENTS

| | | |
|---|---|---|
| CN | 105054932 A | 11/2015 |
| EP | 2906118 B1 | 4/2014 |
| (Continued) | | |

OTHER PUBLICATIONS

Schmeister et al., "Direct Image Reconstruction of Lissajous-Type Magnetic Particle Imaging Data Using Chebychev based Matrix Compression" (Year: 2017).*
(Continued)

*Primary Examiner* — Tung X Nguyen
*Assistant Examiner* — Feba Pothen
(74) *Attorney, Agent, or Firm* — Edell, Shapiro & Finnan, LLC

(57) ABSTRACT

A method for establishing a local concentration distribution of magnetic particles of at least one particle class within an examination volume or a variable derived from this concentration distribution. The method includes providing at least one system matrix, providing MPI signal data of at least one sample including magnetic particles of at least one particle class within a measurement volume, and reconstructing spatially resolved MPI image data from the provided MPI signal data. At least one spatial projection of at least one part of the system matrix is carried out along a projection direction and a projected system matrix is generated thereby. The reconstruction of the MPI image data is implemented with the at least partly projected system matrix, as a result of which MPI image data of a spatial projection of the local concentration distribution of the magnetic particles are produced along the projection direction.

13 Claims, 6 Drawing Sheets

(51) Int. Cl.
*A61B 5/05* (2006.01)
*G01R 33/00* (2006.01)
*G16H 30/20* (2018.01)
*G16H 30/40* (2018.01)
*A61B 90/00* (2016.01)

(52) U.S. Cl.
CPC ............ *G01R 33/00* (2013.01); *G06F 17/16* (2013.01); *G16H 30/20* (2018.01); *G16H 30/40* (2018.01)

(56) References Cited

U.S. PATENT DOCUMENTS

| | | | |
|---|---|---|---|
| 10,338,161 B2* | 7/2019 | Buzug et al. | ...... G01R 33/1276 |
| 2013/0251641 A1 | 9/2013 | Akhtari et al. | |
| 2015/0221103 A1* | 8/2015 | Knopp et al. | ......... G06T 11/005 |
| 2017/0067971 A1 | 3/2017 | Choi et al. | |

FOREIGN PATENT DOCUMENTS

| | | |
|---|---|---|
| WO | 2013088413 A1 | 6/2013 |
| WO | 2015078527 A1 | 6/2015 |
| WO | 2017083643 A1 | 5/2017 |

OTHER PUBLICATIONS

Chae, "Neural network Image Reconstruction for Magnetic Particle Imaging" (Year: 2017).*
Stehnig et al., "Simultaneous Magnetic Particle Imaging . . . ", International Journal on Magnetic Particle Imaging 2, No. 2 (2016).
Grüttner et al., "On the formulation of the image reconstruction problem . . . ", Biomedical Engineering/Biomedizinische Technik; vol. 58, Issue 6 (Dec. 2013).
Knopp et al., "Sparse reconstruction of the Magnetic Particle Imaging System Matrix", EEE Transaction on Medical Imaging; vol. 32 Issue: 8.
Rahmer et al., "First experimental evidence of the feasibility of multi-color magnetic particle imaging", Phys.Med.Biol. 60 (2015).

* cited by examiner

MPI METHOD AND SYSTEM FOR VISUALLY REPRESENTING MPI IMAGE DATA

CROSS REFERENCE TO RELATED APPLICATIONS

This application claims foreign priority under 35 U.S.C. § 119(a)-(d) to German Application No. 10 2018 203 783.3 filed on Mar. 13, 2018, the entire contents of which are hereby incorporated into the present application by reference.

FIELD OF THE INVENTION

The invention relates to a method for establishing a local concentration distribution of magnetic particles of at least one particle class within an examination volume (FOV) or a variable derived from this concentration distribution. The invention also relates to a system for visually representing MPI image data of a spatial projection of a local concentration distribution of magnetic particles or a spatial projection of a variable derived from this concentration distribution in a projection direction.

BACKGROUND

A method for creating spatially projected MPI images is known from [Stehning], for example.

A spatially dependent magnetic field with a field-free region is applied in the case of magnetic particle imaging (MPI) measurements. By applying a magnetic drive field, the field-free region is moved through an examination volume along a trajectory with the aid of a measurement sequence in a drive-field region. The drive-field region is defined by the trajectory and part of the examination volume, with the examination volume (FOV) being defined by the reconstruction region, i.e., the region in which image data are intended to be reconstructed, optionally (e.g., within the scope of an overscan) without selected regions. Signal responses of the magnetic particles are measured as MPI signal data. A reconstruction is carried out to produce MPI image data. In the case of a system-function-based MPI image reconstruction, knowledge of a spatially encoded system response (frequency response), a so-called system function, is necessary, the latter describing the relationship between the measurement signal (MPI signal data) and, for example, the particle distribution of a certain particle class (mapping the particle concentration on a measured frequency response). As a rule, the system function is available as a system matrix. The system matrix is provided for a system matrix region that comprises the part of the image space within which MPI image data should be reconstructed. The system matrix $(SM(r,f))$ provides the basis functions which describe the spatially dependent particle signal response ($\mathcal{F}(u(t))$ or $s(f)$) of the particle concentration distribution $(c(r))$. The system matrix is determined independently of the actual object measurement (e.g., by calibration measurement, by simulation, by hybrid approaches). If the system matrix is determined experimentally (e.g., with a calibration measurement), the particle signal response of an (ideally punctiform) calibration sample is measured at a large number of spatial positions within the system matrix region. This calibration process requires long recording times. On account of the size of the obtained system matrix (system matrix) $(SM(r,f))$, the solution to the reconstruction problem is computationally expensive and time-consuming.

For the purposes of calculating the concentration distribution $(c(r))$ of the magnetic particles in a reconstruction region, a system of equations $\mathcal{F}(u(t))=SM(r,f)\cdot c(r)$ must be solved. The concentration distribution $c(r)$ of the employed magnetic particles within the examination volume can be calculated by suitable reconstruction methods (e.g. [Grüttner]). This step is preferably carried out using a so-called "linear solver" (e.g., Kaczmarz algorithm). Consequently, a particle concentration $(c(r))$ can be determined, for example quantitatively, for each voxel within the drive-field region.

Spatial projections can be produced from the reconstructed MPI image data record to provide the user with a clear image of the object to be examined. This is advantageous for real-time applications, in particular, for example when inserting a catheter into an object. To this end, MPI image data are initially produced in the methods known from the prior art, said MPI image data then being projected along one or more desired projection direction(s) (as a rule, along three orthogonal spatial directions). Thus, the projections are calculated from the reconstructed particle distribution $(c(r))$ in a subsequent operation.

The use of image projections is very useful since 3D image information items can only be represented with difficulties. Thus, the projections serve for an improved representation for the user, who then really looks at a 2D (1D or 0D) image. However, the projected MPI image is obtained with a time delay, which is not suitable, or only suitable to a restricted extent, for a real-time application, on account of the high computational outlay required during the image reconstruction.

SUMMARY

The provision of a method and a system with which a fast image projection is obtained from MPI signal data with as little computational outlay as possible in order thus to facilitate a real-time representation of an MPI image projection is an object of the invention.

According to the invention, this object is achieved by a method according to claim 1 and a system according to claim 12.

The method according to the invention comprises the following method steps:
 providing at least one system matrix;
 providing MPI signal data of at least one sample comprising magnetic particles of at least one particle class within a measurement volume;
 reconstructing spatially resolved MPI image data from the provided MPI signal data.

According to the invention, at least one spatial projection of at least one part of the system matrix is carried out along a projection direction and a projected system matrix is generated thereby. The reconstruction of the MPI image data is implemented through the at least partly projected system matrix, as a result of which MPI image data of a projection of the local concentration distribution of the magnetic particles or of the variable derived from this concentration distribution are produced along the projection direction.

The local concentration distribution of magnetic particles is preferably determined with an MPI installation.

A particle class should be understood to mean magnetic particles that have a certain signal behavior during an MPI measurement, i.e., have a similar signal response behavior. By way of example, different particle classes can differ in terms of the particle type, the particle size, the particle temperature, the ambient conditions, the type of measurement of the particles (e.g., trajectory direction).

According to the invention, a projection operation is undertaken before the MPI image data are reconstructed. Thus, no MPI image data are projected; instead, MPI image data of a projection are reconstructed directly by virtue of the system matrix being initially projected prior to the reconstruction. As a result, the system of equations to be solved during the reconstruction, and hence the computational time required for the reconstruction, is drastically minimized.

Therefore, MPI projection image data that come very close to projection image data produced with known complicated methods can be generated with a reduced computational outlay and time consumption using the method according to the invention. Consequently, the user can obtain projected real-time images.

The projected system matrix has an improved SNR compared to the original system matrix. This may be advantageous, particularly in the case of calibration measurements with a small punctiform sample.

Preferably, the entire system matrix is projected such that the projected system matrix has one dimension less than the original system matrix. However, it is also possible to not completely project the system matrix such that the corresponding projected system matrix is smaller overall, but extends over the same number of dimensions (reduction in the size of the system matrix in one dimension). By way of example, this can be implemented by virtue of in each case half of the voxels of one row of the system matrix being projected onto a voxel (the result would then be one dimension with two voxel rows) or by virtue of only projecting voxels situated at a certain position within the system matrix (e.g., it would be conceivable for edge voxels of the system matrix to be projected on a voxel but voxels in the center not being projected at all).

Since information items can be lost by the projection along an inexpedient projection direction, it is advantageous if a plurality of projections are carried out in different projection directions, preferably along three orthogonal spatial directions. Here, the projection of the system matrix in a first projection direction is independent of the projection of the system matrix in each further projection direction. Different projections, and MPI image data reconstructed therefrom, can therefore be calculated at the same time.

In a specific variant, the projection direction is varied during the MPI measurement. Consequently, the projection can always be in an anatomically expedient direction, for example. In order to further reduce the computational outlay during the reconstruction, provision can be made for only selected frequency components of the system matrix to be used for the projection and/or reconstruction.

In particular, provision can be made for only frequency components of the system matrix whose signal-to-noise ratio lies above a threshold value to be used for the reconstruction.

Moreover, there is the option of only reconstructing MPI image data from selected regions of the examination volume. Thus, only a portion of the examination volume is projected in this case. By way of example, regions with a high particle concentration can be selected. In order to mask regions of the examination volume for the reconstruction, regions can be removed from the system matrix or the corresponding voxels of the system matrix can be set to zero. Hence, only the desired voxels are included in the system of equations and reconstructed. However, artifacts could occur should particles still be situated outside of the reconstructed volume.

In a specific variant, the reconstruction is implemented in the sparse domain [Knopp]. To this end, the system matrix is projected first; each of the projections is transformed thereafter.

Preferably, the system matrix is measured with an MPI calibration measurement. In the case of such an experimental determination of the system matrix, the particle signal response of an (ideally punctiform) sample is measured at a large number of spatial positions within a system matrix region which comprises the examination volume.

As an alternative thereto, the system matrix can be simulated. Combining both methods is possible; the experimentally obtained data can be used here as sampling points for a system matrix simulation. (A reduced number of measurements for a better simulation.)

The established system matrix can be generated/have been generated from at least two system matrices linked by a mathematical operation. Thus, the system matrix employed for the projection need not necessarily be the system matrix that describes the spatially dependent particle signal response of particles of a certain particle class. Rather, the system matrix employed for the method according to the invention can also arise from combining one such system matrix with one or more other measured or simulated system matrices, e.g., from adding two system matrices for different particle classes. The system matrix established thus then describes the spatially dependent particle signal response of particles of different particle classes, from which the overall concentration distribution can then be established.

In a specific variant, at least two system matrices are established; respectively one projected system matrix is generated for each system matrix, wherein the projections of the system matrices are implemented along the same projection direction. The projected system matrices are appended. The MPI image data are reconstructed using the projected and appended system matrix. In this way, it is possible to generate MPI image data of a projection for two different particle systems (projected multi-parameter image data records).

The invention also relates to a system for visually representing MPI image data of a projection of a local concentration distribution of magnetic particles or a projection of a variable derived from this concentration distribution in at least one projection direction. The system according to the invention comprises:

i) an MPI installation for detecting MPI signal data,
ii) an electronic storage medium containing at least one projected system matrix or a stored computer program configured to generate at least one system matrix projected along a projection direction,
iii) a stored computer program, though which reconstruction of the MPI image data using the projected system matrix is performed, and
iv) an indicator apparatus, in particular a display, which represents the reconstructed MPI image data.

The system according to the invention allows the reconstruction and representation of MPI image data in real time.

Preferably, the system according to the invention is configured in such a way that the above-described method can be carried out with the system. Consequently, the system must be able to carry out a projection of the system matrix along a projection direction (in particular, a stored computer program configured to generate a system matrix projected along a projection direction).

Further advantages of the invention emerge from the description and the drawing. Likewise, according to the invention, the features specified above and the features yet to be explained below can find use either respectively on their own or together in any combination. The shown and described embodiments should not be understood as a comprehensive list but instead have an exemplary character for illustrating the invention.

DETAILED DESCRIPTION

Figure 1:
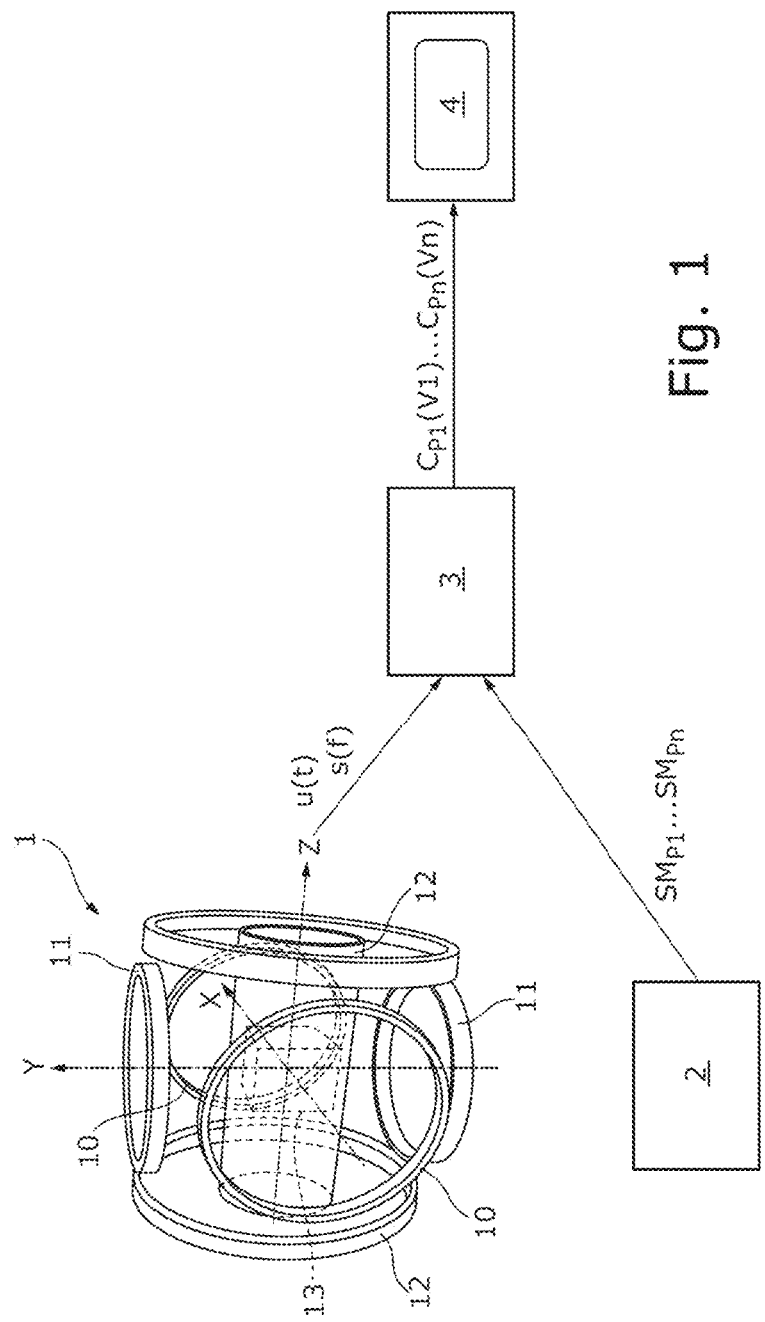
FIG. 1 shows a schematic illustration of a system according to the invention.
Figure 3:
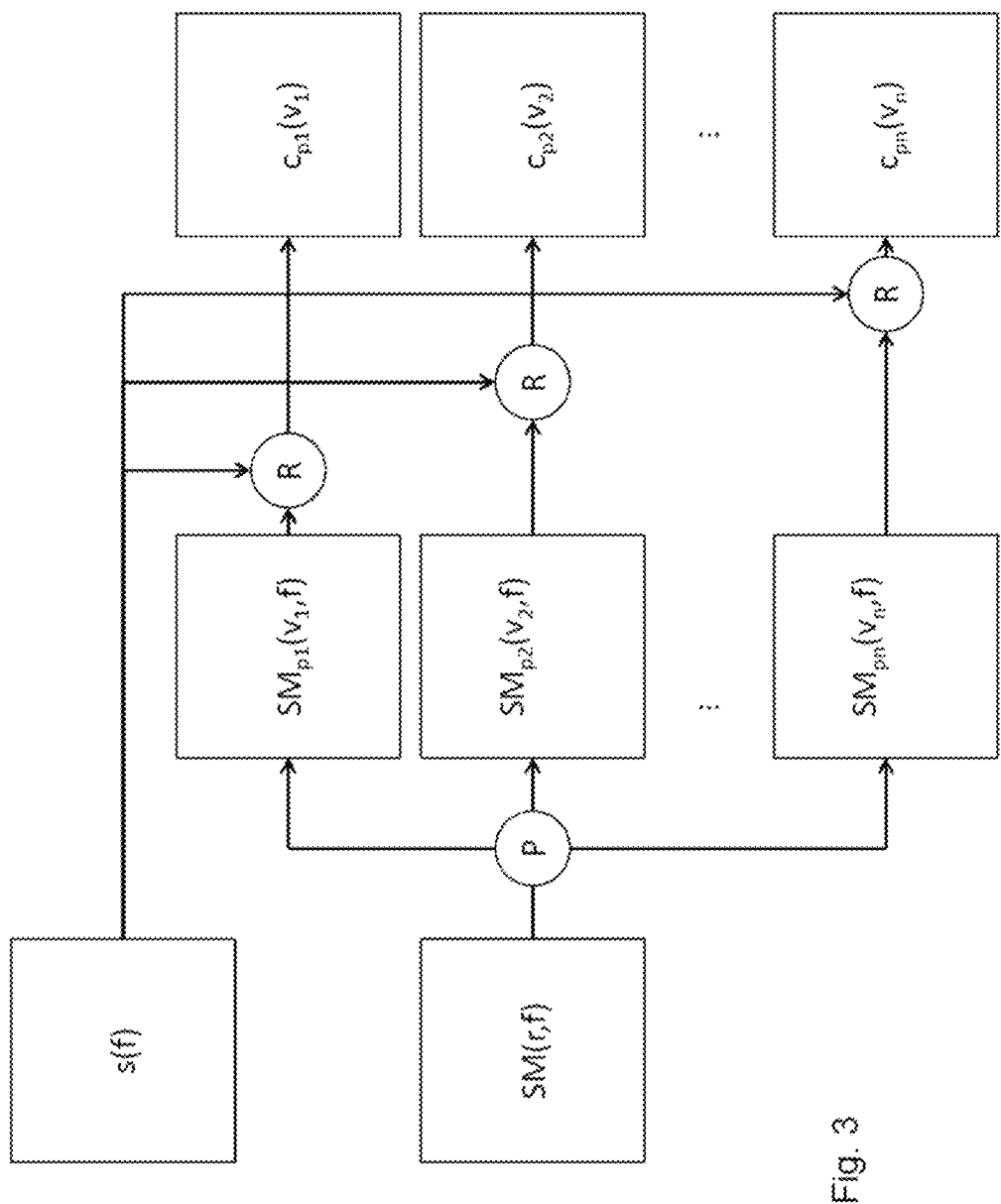
FIG. 3 shows a flowchart of the method according to the invention.

The system according to the invention is shown in FIG. 1 and comprises an MPI installation 1 with coil arrangements 10, 11, 12 for producing a spatially dependent magnetic field and a magnetic drive field within an examination volume 13, as is known from U.S. Pat. No. 9,364,165 B2, for example. MPI signal data u(t) (signal data in the time domain) or s(f) (signal data in the frequency domain) are detected by the MPI installation 1. Moreover, the system according to the invention comprises a device 2 for providing projected system matrices $SM_{P1} \ldots SM_{Pn}$. The projected system matrices $SM_{P1} \ldots SM_{Pn}$ and the MPI signal data u(t) or s(f) are fed to a reconstruction device 3 (e.g., a linear solver) for reconstructing MPI image data $c_{P1}(v_1) \ldots c_{Pn}(v_n)$ from the MPI signal data u(t) or s(f) and the projected system matrices $SM_{P1} \ldots SM_{Pn}$, as shown in FIG. 3. The MPI image data $c_{P1}(v_1) \ldots c_{Pn}(v_n)$ are presented on an indicator apparatus 4 of the system according to the invention. The device 2 for providing a projected system matrix can be an electronic storage medium, in which a projected system matrix is stored, or a stored computer program that can be used to generate the projected system matrix along a projection direction.

Figure 2:
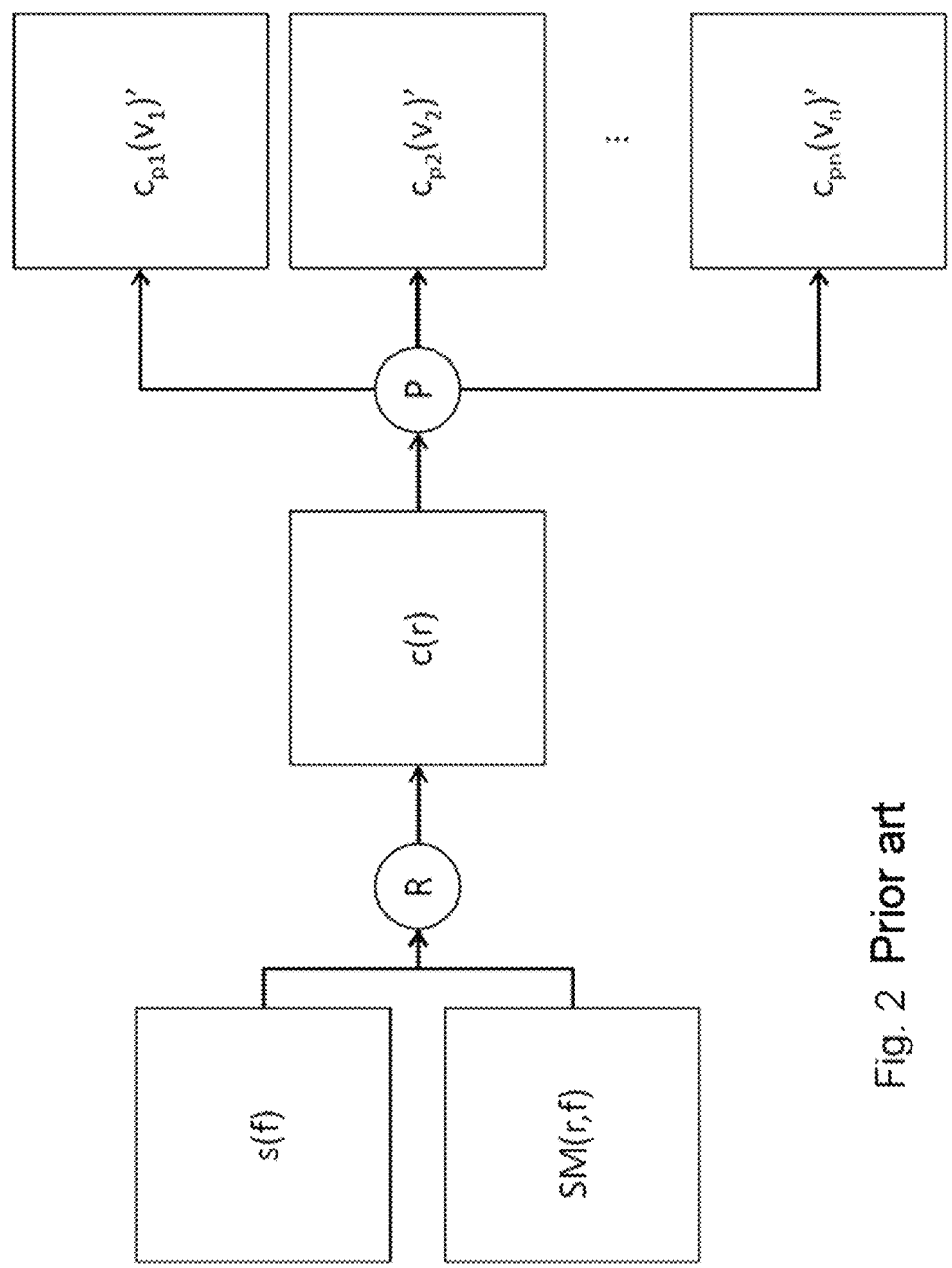
FIG. 2 shows a flowchart of a method for generating projected MPI image data according to the prior art.

FIG. 2 shows the procedure of a method according to the prior art, in which an MPI image data record c(r) is initially produced with the aid of MPI signal data s(f) and a system matrix SM(r,f) within the scope of a reconstruction operation R. Then, image projections $c_{P1}(v_1)' \ldots c_{Pn}(v_n)'$ can be produced along different projection directions within the scope of a projection operation P.

The method according to the invention is illustrated in FIG. 3. Here, the projection operation P is carried out before the reconstruction operation R. The system matrix SM(r,f) can be projected along at least one projection direction, as a result of which projected system matrices $SM_{P1}(v_1,f) \ldots SM_{Pn}(v_n,f)$ are generated. These projected system matrices $SM_{P1}(v_1,f) \ldots SM_{Pn}(v_n,f)$ are then used for the reconstruction operation R to reconstruct the MPI image data $c_{P1}(v_1) \ldots c_{Pn}(v_n)$ from the MPI signal data s(f). This reduces the amount of data used for the reconstruction operation R, even when a plurality of projected system matrices $SM_{P1}(v_1,f) \ldots SM_{Pn}(v_n,f)$ are produced.

Figure 4:
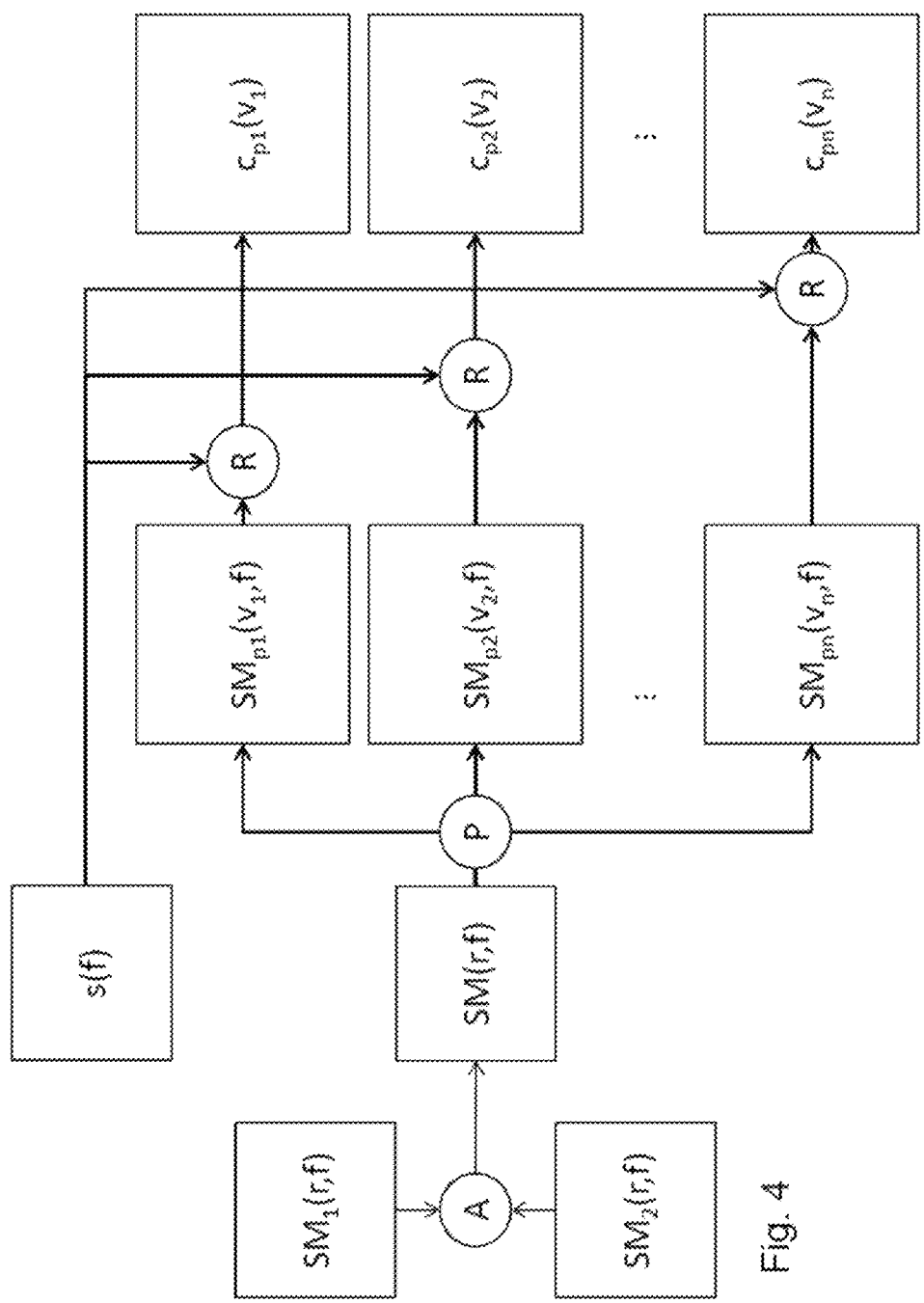
FIG. 4 shows a flowchart of a specific variant of the method according to the invention, in which a linked system matrix is used.

FIG. 4 shows a specific variant of the method according to the invention, in which the system matrix SM(r,f) is not directly measured or simulated but instead obtained by mathematical operation (in this case: addition) applied to two system matrices $SM_1(r,f)$, $SM_2(r,f)$ and subsequently subjected to the projection operation P. In this way, projections of the local overall concentration distribution of magnetic particles can be established independently of the particle class. Such a projection of the local overall concentration distribution can be helpful, for example for observing a catheter to be inserted into a vein, since the catheter tip may be coated with magnetic particles of different particle classes (e.g., different particle sizes) and all magnetic particles applied to the catheter tip should contribute to localizing the catheter tip. By combining the system matrices $SM_1(r,f)$, $SM_2(r,f)$ prior to the projection operation, the computational outlay is further reduced.

Figure 5:
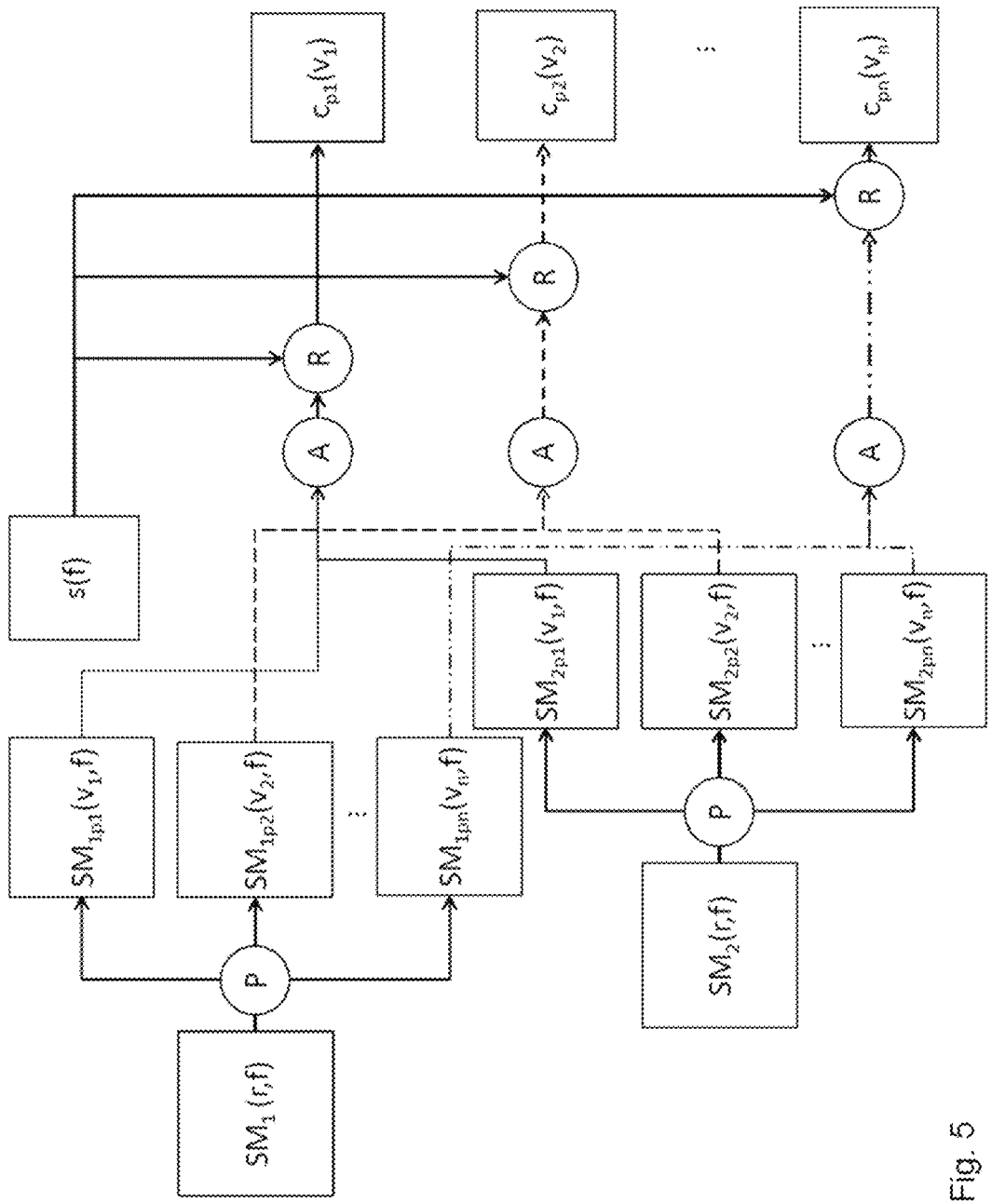
FIG. 5 shows a flowchart of a further specific variant of the method according to the invention, in which projections are reconstructed for different particle classes.

FIG. 5 shows a further variant of the method according to the invention, in which projections are created for a multi-parameter space. To this end, a system matrix $SM_1(r,f)$, $SM_2(r,f)$ is established in each case for different particle classes (e.g., for different particle types). The desired number n of spatial projections $SM_{1p1}(v_1,f)$, $SM_{1p2}(v_2,f)$, ..., $SM_{1pn}(v_n,f)$; $SM_{2p1}(v_1,f)$, $SM_{2p2}(v_2,f)$, ..., $SM_{2pn}(v_n,f)$ is generated for each system matrix $SM_1(r,f)$, $SM_2(r,f)$. The projected system matrices that were projected along the same projection direction are appended and form an extended (appended) projected system matrix (not illustrated). In the shown example, n projected system matrices are generated for two $SM_1(r,f)$, $SM_2(r,f)$, said projected system matrices then being used to form n appended projected system matrices. Thus, the appended projected system matrices each consist of two projected system matrices, which result from projections of different system matrices along the same projection direction. Finally, the appended projected system matrices are used to reconstruct the MPI image data $cp_1(v1)$, $cp_2(v2)$, $cp_3(v3)$, with the MPI image data having a plurality of (in this case: two) sub-projections. Each sub-projection comprises image data of a particle class for the same predetermined examination volume (multi-parameter space). Thus, for example, the concentration of particles of a certain particle class within the examination volume can be represented in a sub-projection.

Figure 6A:
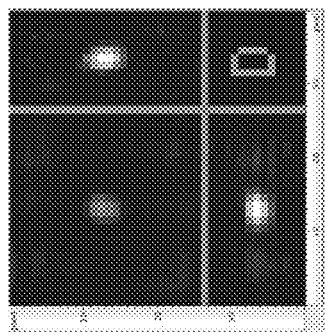
FIG. 6A shows projections of MPI image data, generated using a method according to the prior art.
Figure 6B:
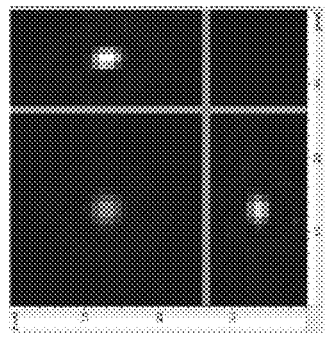
FIG. 6B shows MPI image data of projections, generated using the method according to the invention.

FIG. 6A shows MPI image data of projections that were produced through a known method (FIG. 6A) and FIG. 6B shows the method according to the invention (FIG. 6B). Shown here is the reconstruction of a 3D data record of a punctiform sample, in each case projected in the Z- (top left), X- (top right) and Y-directions (bottom left). Only very minor differences in the shown 2D images can be made out between the method according to the prior art and the method according to the invention. This shows that reliably projected image data can be established using the method according to the invention, for example for real-time measurements.

CITATIONS

[Stehning] Stehning et al. "Simultaneous Magnetic Particle Imaging (MPI) and Temperature Mapping Using Multi-Color MPI." International Journal on Magnetic Particle Imaging 2, no. 2 (2016).
https://journal.iwmpi.org/index.php/iwmpi/article/view/34; FIG. 6

[Grüttner] Grüttner et al. "On the formulation of the image reconstruction problem in magnetic particle imaging"; Biomedical Engineering/Biomedizinische Technik; Volume 58, Issue 6 (December 2013); DOI: https://doi.org/10.1515/bmt-2012-0063)

[Knopp] Knopp et al. "Sparse Reconstruction of the Magnetic Particle Imaging System Matrix" EEE Transactions on Medical Imaging; Volume: 32 Issue: 8; DOI: 10.1109/TMI.2013.2258029

U.S. Pat. No. 9,364,165 B2

LIST OF REFERENCE SIGNS

1 MPI installation
2 Device for providing projected system matrices
3 Reconstruction device (linear solver)
4 Indicator apparatus
11, 12, 13 Coil arrangements
14 Examination volume
c(r) MPI image data record
$c_{P1}(v_1) \ldots c_{Pn}(v_n)$ MPI image data of the projections
$c_{P1}(v_1)' \ldots c_{Pn}(v_n)'$ Projected MPI image data according to the prior art
P Projection operation
R Reconstruction operation
A Addition parameter
SM(r,f) System matrix
$SM_{P1}(v_1,f) \ldots SM_{Pn}(v_n,f)$ Projected system matrices
u(t) MPI signal data (time domain)
s(f) MPI signal data (frequency domain)

What is claimed is:

1. A method for establishing a local concentration distribution of magnetic particles of at least one particle class within an examination volume or a variable derived from the local concentration distribution, comprising:
    providing at least one system matrix;
    providing magnetic particle imaging (MPI) signal data, from an MPI installation, of at least one sample comprising the magnetic particles of at least one particle class within a measurement volume;
    performing, by a device for providing a projected system matrix, at least one spatial projection of at least one part of the system matrix along a projection direction, to generate a projected system matrix; and
    reconstructing, with a reconstruction device, a spatially resolved MPI image data from the provided MPI signal data,
wherein the reconstructing of the MPI image data is implemented with the at least partly projected system matrix, whereby the MPI image data of a spatial projection of the local concentration distribution of the magnetic particles or of the variable derived from the local concentration distribution are produced along the projection direction.

2. The method as claimed in claim 1, further comprising performing further spatial projections in different projection directions.

3. The method as claimed in claim 1, further comprising varying the projection direction during MPI measurement.

4. The method as claimed in claim 1, wherein only selected frequency components of the system matrix are used for the spatial projection and/or the reconstruction.

5. The method as claimed in claim 4, wherein the selected frequency components of the system matrix used for the reconstruction are only those whose signal-to-noise ratio lies above a threshold value.

6. The method as claimed in claim 1, wherein only MPI image data from selected regions of the examination volume are used for the reconstruction.

7. The method as claimed in claim 1, wherein the reconstruction is implemented in a sparse domain.

8. The method as claimed in claim 1, wherein the system matrix is measured with an MPI calibration measurement.

9. The method as claimed in claim 1, wherein the system matrix is simulated.

10. The method as claimed in claim 1, wherein the system matrix is generated from at least two system matrices linked by a mathematical operation.

11. The method as claimed in claim 1, wherein
    providing the at least one system matrix comprises establishing at least two system matrices and generating respectively the projected system matrix for the system matrices, wherein the spatial projections of the system matrices are implemented along a same projection direction,
    wherein the method further comprises appending the projected system matrices, and
    wherein the MPI image data are reconstructed with the projected and appended system matrix.

12. A system for visually representing MPI image data of a spatial projection of a local concentration distribution of magnetic particles or a spatial projection of a variable derived from the local concentration distribution in a projection direction, comprising:
    an MPI installation configured to detect MPI signal data,
    a non-transitory electronic storage medium containing: a projected system matrix or a stored computer program configured to generate a system matrix projected along a projection direction, and a stored computer program, configured to reconstruct the MPI image data with the projected system matrix,
and
    an indicator apparatus configured to display the reconstructed MPI image data in real-time.

13. The system as claimed in claim 12, further configured to establish the local concentration distribution of magnetic particles of at least one particle class within an examination volume or a variable derived from this concentration distribution, comprising:
    providing the system matrix;
    providing the MPI signal data of at least one sample comprising magnetic particles of at least one particle class within a measurement volume;
    performing at least one spatial projection of at least one part of the system matrix along a projection direction, to generate a projected system matrix; and
    reconstructing spatially resolved MPI image data from the provided MPI signal data,
wherein the reconstructing of the MPI image data is implemented with the at least partly projected system matrix, whereby the MPI image data of a spatial projection of the local concentration distribution of the magnetic particles or of the variable derived from this concentration distribution are produced along the projection direction.

* * * * *